(12) United States Patent
Tomassini et al.

(10) Patent No.: US 6,998,394 B2
(45) Date of Patent: Feb. 14, 2006

(54) PROCESS FOR ISOLATING PHYSALINS FROM PLANTS AND PHARMACEUTICAL COMPOSITIONS CONTAINING PHYSALINS

(75) Inventors: Therezinha C. B. Tomassini, Rio de Janeiro (BR); Ricardo R. Dos Santos, Bahia (BR); Milena B. P. Soares, Bahia (BR); Deise Cristina D. Xavier, Rio de Janeiro (BR); Nancy S. Barbi, Rio de Janeiro (BR); Ivone Maria Ribeiro, Rio de Janeiro (BR); Renata O. de A. Soares, Rio de Janeiro (BR); Edmir Fernandez-Ferreira, Rio de Janeiro (BR)

(73) Assignee: Fundacao Oswaldo Cruz - FIOCRUZ, Rio de Janeiro (BR)

( * ) Notice: Subject to any disclaimer, the term of this patent is extended or adjusted under 35 U.S.C. 154(b) by 39 days.

(21) Appl. No.: 10/403,003

(22) Filed: Apr. 1, 2003

(65) Prior Publication Data

US 2005/0101519 A1    May 12, 2005

Related U.S. Application Data

(62) Division of application No. 09/417,779, filed on Oct. 14, 1999, now abandoned.

(30) Foreign Application Priority Data

Jul. 23, 1999  (BR) .................................... 9904635
Sep. 28, 1999  (BR) .................................... 9904363

(51) Int. Cl.
    A61K 31/56    (2006.01)
(52) U.S. Cl. ..................................... 514/169
(58) Field of Classification Search ................ 424/489; 514/169
    See application file for complete search history.

(56) References Cited

U.S. PATENT DOCUMENTS 5,766,632 A * 6/1998 Oldham et al. ............. 424/486

OTHER PUBLICATIONS

Chiang et al., Anticancer Research, vol. 12, pp. 1155-1162, 1992.
Lin et al., American J. Chinese Medicine, vol. 20(3-4), pp. 233-243, 1992.

* cited by examiner

Primary Examiner—Alton Pryor
(74) Attorney, Agent, or Firm—Nixon & Vanderhye P.C.

(57) ABSTRACT

The present invention relates to a process for obtaining *Physalis angulata* extracts, particularly to isolate ergostane-type steroidal derivatives, such as physalins, which are useful in the treatment of infections caused by protozoans. The physalins of the invention have also prophylactic and therapeutic properties for treating auto-immune diseases in mammals.

The isolation process to obtain physalins comprises the steps of: (a) grinding roots, leaves or stem-bark of *Physalis* ssp; (b) extracting the material obtained in step (a) with solvents selected from the group consisting of water and alcohols, such as methanol, ethanol, 1-propanol, 2-propanol, isobutanol; (c) evaporating the extract obtained in step (b) and washing the syrup material with a suitable solvent; (d) rapid filtering of the extract of step (c) and fractionating the components of the extract according to a polarity gradient of organic solvents; and (e) separating the steroidal components contained in the fractions by chromatography.

12 Claims, 6 Drawing Sheets

PROCESS FOR ISOLATING PHYSALINS FROM PLANTS AND PHARMACEUTICAL COMPOSITIONS CONTAINING PHYSALINS

This application is a divisional of application Ser. No. 09/417,779, filed Oct. 14, 1999, now abandoned the entire contents of which is incorporated herein by reference.

The present invention relates to a process for obtaining *Physalis angulata* extracts, particularly to isolate ergostane-type steroidal derivatives, such as physalins, which are useful in the treatment of infections caused by protozoan parasites. According to the invention, physalins have also prophylactic and therapeutic properties for treating autoimmune diseases in mammals.

BACKGROUND OF THE INVENTION

Withanolides are ergostane-type steroids that have been isolated mainly from plants of the family Solonaceae and, specifically, from genera Withania, Duralia, Datura, Jaborosa, Physalis, Deprea and Nicandria. Throughout the world there are many folk applications of these plants. Their extracts, for example, are used in the treatment of asthma, hepatic diseases, several inflammatory processes and cancer, and even as a hypnotic drug. Withjardin A, B, C and D and derivatives thereof are withanolides isolated from leaves and stems of *Deprea orinocensis* and can be used as immunomodulators of the immune system (see Patent U.S. Pat. No. 5,681,950).

Physalins are steroidal constituents of *Physalis* spp. which belongs to the Solanaceae family and are characterized by their modified ergostane-type framework, being 16,24-cyclo-13,14-secosteroids. The most studied species are: *P. angulata, P. alkekengi var francheti, P. ixocarpa, P. laninfolia, P. minima, P. peruviana, P. phyladelphia, P. pubescens* and *P. viscosa*. As a result of their polyfunctional structures, physalins can be classified as the most advanced group in terms of the biogenetic oxidation level among withasteroids.

Physalins are normally present at levels of 30 to 500 ppm in root and epigeal parts of *Physalis* species. *P. angulata* is an annual herb widely grown through the North and Northeast of Brazil (Braga, R., Plantas do Nordeste, especialmente do Ceará, Mossoró, Brasil, ESAM, 540, 1976) and is popularly known as "Bate-Testa", "Bucho de Rã", "Mata-Fome", "Juá" or "Juá de Capote" and more frequently, "Camapú" (Pio Corrêa, Dicionário das Plantas úteis do Brasil e das exóticas cultivadas, R10 de Janeiro, Min. da Agricultura, Vol. I, pp. 10, 1962).

Crude extracts from *Physalis* species are reported to have been used in indigenous medicine systems. It is also mentioned by Sanchez et al (Sanchez, E. G., Silva, M. T. G., Ribeiro, I. M., Tomassini, T. C. B., Evolutions of the antibacterial activity of *Physalis angulata* L., in Abstracts of the 1$^{st}$ Congress of Pharmaceuticals Sciences, Ribeirao Preto, S. Paulo, Brasil,—Index. Bolletino Chimico Farmaceutico, Vol. 136, pp. 154, 1997) that *Physalis* extracts and their isolated constituents exhibit biological activity, including the anti-bacterial effect of *P. angulata* extracts from root, leaf and stem-bark.

Chiang et al (Chiang, H. C., Jaw, S. M., Chen, C. F. e Kan, W. S., Anticancer Research 12, 837, 1992.) demonstrated that physalins A, D, F e L extracted from *Physalis* species have been shown to be active against human tumors like hepatoma, cervix uteri, lung and colon cells in vivo and in vitro tests.

As described in U.S. Pat. No. 5,135,746 the use of active compounds extracted from plants with pharmacological activity have been used for the prophylactic and therapeutic treatment of protozoal diseases, such as malaria and amebic dysentery from old times.

Conventionally used agents for the treatment of protozoal diseases caused by the genera *Trypanosoma* and *Leishmania* are quite unsuitable for widespread use due to its unpleasant side-effects, primarily nausea, vomiting and allergic reactions, and to some cases of drug resistance.

Chagas Disease, caused by infection with the parasite *Trypanosoma cruzi*, is responsible for the infection of 16–18 million people. Moreover, some 100 million people—a quarter of all the inhabitants of Latin America—are at risk of contracting the disease (Tropical Disease Research, World Health Organization, pp. 125–133, Geneva, 1995).

The disease usually begins as an acute infection in childhood, which may last up to two months, followed by a slow, chronic inflammatory process, which in around a quarter of those infected damages the autonomous nervous tissues of the heart, a condition which in turn may cause heart failure and premature death in mild life.

Unfortunately, no treatment is available for the chronic forms of the disease. Nifurtimox, a nitrofuran derivative, and benzinidazole, a nitroimidazole, are oral synthetic drugs used in acute cases, but their efficacy varies considerably from place to place, perhaps due to variation in parasite strains. The drugs must be taken daily for long periods. Both drugs can produce unpleasant side-effects, allergic reactions and nauseas.

Plant extracts and/or its isolated components may be an alternative for commercial drugs used for treating Chagas Disease. As an example of this approach, it may be cited the document U.S. Pat. No. 5,290,553 which describes the use of purified extracts and alkaloids from *Picralima nitida* and *Dorstenia multiradiata* in mammals infected with *Trypanosoma brucei brucei*.

Another example of medicinal plants with trypanocidal activity was described by Freiburghaus et al (Freiburghaus, F., Kaminsky, R., Nkunya, M., H., H., e Brun, R., "Evaluation of African medicinal plants for their in vitro trypanocidal activity", J. Of Ethnopharmacology, 55, pp. 1–11, 1996). The authors screened 24 plant extracts commonly used in african traditional medicine for the treatment of Human African trypanosomiasis (sleeping sickness) caused by *Trypanosoma brucei rhodesiense*. The most active extracts with $IC_{50}$ values below 1 μg/ml were derived from *Annona senegalensis, Bussea occidentalis* and *Physalis angulata*. Compared to $IC_{50}$ values of commonly used trypanocidal drugs, e.g. suramin at a concentration of 10.7 ng/ml, the values even for active extracts were high. However, since the crude plant extracts used are mixtures of various compounds, purification or active extracts might result in a considerable increase in activity.

It is important to emphasize that neither these plant extracts nor their contents were tested against *T. cruzi*, the causative agent of Chagas Disease.

When untreated sleeping sickness eventually gives no respite from suffering, day or night, and ends in death (WHO, 1994). It affects 250 000 to 300 000 people per year. The causative agents are *Trypanosoma brucei rhodesiense* in East Africa and *Trypanosoma brucei gambiense* in West and Central Africa.

The available drugs used in the treatment of sleeping sickness are suramin, pentamidine, melarsoprol and difluoromethylornithine (DEMO) and may cause severe side effects. Moreover, these drugs do not present any effect against *Trypanosoma cruzi* and, consequently, are not used in the treatment of Chagas Disease.

Consistently, both parasites and drugs used for the treatment of Chagas Disease and Sleeping Sickness are distinct. In fact, different species or strains may cause different diseases. So, it is unpredictable to forsee that the efficacy of a medicament used to treat Sleeping Sickness remain the same when dealing with Chagas Disease.

Infections due to protozoa of the genus *Leishmania* are also a threatened world-wide health problem with high endemicity in developing countries. *Leishmania* infections are zoonosis globally affecting individuals. Approximately 400 million people within 80 countries are at risk of contracting the disease, 12 million are already infected in the world and the disease growing rate being about 600 thousand new cases a year (WHO, 1994). The pathological effects of the disease are complex and manifests itself as various forms ranging from self-healing cutaneous lesions, post-kala-azar dermal leishmaniasis, disfiguring mucocutaneous and diffuse cutaneous diseases to fatal systemic infection caused by visceral leishmaniasis (*Kala azar*).

Leishmanias are digenetic protozoas which invade the macrophages of the host and have a complex life cycle based on two different hosts and two distinct evolution cycle. The promastigote form is elongated having a free anterior flagellum which lives in a vector while the amastigote has an ovoid shape without free flagellum and may be found intracellularly in vertebrate hosts. The vector is a group of more than 50 species and sub-species of insects belonging to the genera *Lutzomyia*, occuring largely in the Americas, and *Phlebotomus* which may be found elsewhere.

At the present time, the clinical drug intervention is limited primarily to the use of pentavalent antimonials, sodium stibogluconate and N-methylglucamine antimonate, and secondarily to amphotericin or pentamidine. These antileishmanials require parenteral administration with clinical supervision or hospitalization during treatment because of the severity of possible toxic side-effects that include cardiac and/or renal failure.

The treatment with the aforementioned agents is not consistently effective, particularly for the most virulent leishmanial disease forms. The World Health Organization has reported large scale resistance of kala-azar to pentavalent antimonials which are the preferred chemotherapy for the treatment of the most forms of leishmanial disease (TDR News. December. 1990). In some endemic regions, it has been observed that prolonged medication (22 months or more) with pentavalent antimonials is required to effect a clinical cure. However, long term therapy with this class of drugs is not usually justifiable due to the mentioned cardiac and renal toxicity of pentavalent antimonials.

In this context, a great effort has been made in order to identify natural products with leishmanial activity. Berberine, an isoquinolinic alkaloid, has been shown to possess significant leishmanicidal activity. This substance can be found in the *Berberis aristat* specie and is largely used in popular medicine for the treatment of leishmaniasis and other diseases caused by protozoans. According to Iwu et al (Iwu, M. M., Jackson, J. E. and Schuster, B. G. (1994). "Medicinal plants in the fight against Leishmaniasis. Parasitol. Today. 10(2): 65–68), experiments proved that this drug possess a great leishmanicidal activity, in vivo and in vitro, against lots of *Leishmania* species.

U.S. Pat. No. 5,290,553 describes alkaloid extracts from seeds, fruit-rind and stem-bark and new isolated alkaloids from *Picralima nitida*, and alkaloid extracts from seeds, fruit-rind and stem-bark of plants selected from the group consisting of *Gongronema latifolia, Rothmania withfieldii* and *Desmodium gangeticum* used for the treatment of protozoal diseases including leishmanial infections in mammals.

Concerning to auto-immune diseases, such as SLE (systemic lupus erythematous), rheumatoid arthritis, auto-immune thyroiditis, Sjøgren's syndrome, idiopathic thrombocytopenic purpura and haemolytic anaemia, many treating substances have been proposed. In U.S. Pat. No. 4,701,450, it is described the use of pharmaceutical preparations based on steroids, particularly oestrene derivatives, as immunomodulators. U.S. Pat. No. 5,276,013 refers to compositions for treating the auto-immune disease systemic lupus erythematosus, the compositions being related to conjugates of biologically stable valency platform molecules such as polymers, preferably copolymers of glutamic acid and D-lysine or polyethylene glicol and certain polynucleotides that have been found to be effective for inducing tolerance to self-antigens involved in SLE.

Some individuals acquire auto-immune diseases due to failure in immune tolerance mechanism which may be defined as a permanent form of immunesupression that keeps individuals from reacting with their own tissues.

Auto-immune diseases are typically treated with broad spectrum, nonspecific immunosuppressants such as cyclophosphamide or prednisone. But these drugs cause deleterious side-effects related with suppression of all aspects of the immune system, thus causing the inhibition of its essential and beneficial functions. Consequently, these drugs must be administered with extreme caution and are not always appropriate to manage the disease on a continuing basis. In fact, severely immunosuppressed individuals by drug treatment are at risk for other complications, especially infectious diseases.

Accordingly, there is a great need for a more effective and mild anti-parasite drug without the disadvantages of the available chemotherapeutic agents which are toxic and drug resistance are becoming widespread. There is also a need for immunomodulators capable of reestablishing immune tolerance to the autoantigens without affecting the normal functions of the immune system. Such an improved drug may be used in a lower concentration and must provide a higher survival inhibition. This can be accomplished by using plant extracts and more particularly its steroid derivatives components.

SUMMARY OF THE INVENTION

The object of the present invention is the use of ergostane-type steroids, named physalins, and to alcoholic and aqueous extracts from *Physalis* species in the treatment of infections caused by protozoans. As immunosuppressors, physalins and *Physalis* extracts may also be used for treating auto-immune diseases.

In one embodiment, the present invention relates to a pharmaceutical composition having one or more physalin(s) in combination with a pharmaceutically acceptable carrier.

In another embodiment of the present invention, there is provided a pharmaceutical composition having physalin B or physalin D in combination with a pharmaceutically acceptable carrier.

Other embodiment of the present invention provides a pharmaceutical composition having an alcoholic steroid extract from *Physalis* species combined with a pharmaceutically acceptable carrier.

Another embodiment of the present invention provides a pharmaceutical composition having an aqueous steroid extract from *Physalis* species combined with a pharmaceutically acceptable carrier.

In another embodiment, the present invention provides an isolation process to obtain physalins comprising the steps of: (a) grinding roots, leaves or stem-bark of *Physalis* ssp; (b) extracting the material obtained in step (a) with solvents selected from the group consisting of water and alcohols, such as methanol, ethanol, 1-propanol, 2-propanol, isobutanol; (c) evaporating the extract obtained in step (b) and washing the residue with a suitable solvent; (d) rapid filtering of the extract of step (c) and fractionating the components of the extract according to a polarity gradient of organic solvents; and (e) separating the steroidal components contained in the fractions by chromatography.

DETAILED DESCRIPTION OF THE INVENTION

As mentioned before, several trypanocidal and leishmanicidal drugs are currently been used in endemic areas. However, these drugs are highly toxic and depending on the dosage and frequency of treatment, children are the most likely victims.

The "ideal drug" would achieve parasitological cure of both acute and chronic cases from all parts of Latin America (Tropical Disease Research, World Health Organization pp. 125–133, Geneva, 1995). This "ideal drug" should: (i) be effective by the oral and, for cases of mega-oesophagus, the parenteral route; (ii) be effective in one or a small number of daily doses; and (iii) be affordable by those who suffer from the disease. At the doses used, it would be free of serious side-effects and of teratogenicity. In addition, it would not require patients to be hospitalized, and drug resistance would not develop rapidlly.

But until now, despite intensive research and many leads, nothing had come close to the requirements for Chagas Disease set in an expert meeting in Washington, D.C., in 1981, and the health system is still left only with the original and unsatisfactory drugs, nifurtimox and benznidazole. Moreover, there is a consensus that patients in the chronic stage of the disease, with overt lesions, do not benefit from trypanocidal treatment. Symptomatic treatment appears to be all that can be offered.

Referring to the auto-immune diseases, nonspecific immunosuppressants must be used with extreme caution in order to avoid complications related with severe immunossupression.

Thus, in order to come closer to the "ideal drug" and to the requirements set forth above, the present invention proposes new pharmaceutical compositions based on one or more physalins as active anti-protozoan and immunosuppressive substances, at concentrations ranging from about 10 to about 50%, for the treatment of protozoan infections. Moreover, in another embodiment of the present invention, it is described a novel isolation process to obtain physalins from plants.

Physalins belong to the group of C-28 ergostane-type compounds: 13,14-seco-16,24-cyclosteroid derivatives having the characteristics of: a) two lactones, γ and δ, in positions 13–20 and 22–24; b) an α, β unsaturated ketone at A ring; c) an ether ring between carbons 14 and 17; d) a ketone at C-15, e) an α-hydroxyl group at C-13 and f) optionally an oxyrane bridge between carbons 14–27. The main characteristic of those steroids is the presence of 13,14-seco-16,24 cyclowithanolide framework or skeleton (Glotter, E., Withanolides and related ergostane type steroids, Nat. Prod. Rep., 8: 415, 1994).

Nineteen physalins (A to S) are known and they are divided into 8 chemotypes: a) chemotype I is represented by physalins A and C, b) chemotype II by physalins L, M and O, c) chemotype III contains physalins B, D, E, F, H, I, J and N, d) chemotype IV by physalin G, e) chemotype V by physalins K and Q, f) chemotype VI physalin P, g) chemotype VII is represented by physalin S, and h) chemotype VIII by physalin R. Physalins A, B and Q correspond to the matrices of skeletons that lead to the biosynthesis of the other related substances. Physalin B is the biogenetic precursor of the majority of the other physalins. The structures of the physalins are hereinafter presented.

physalin A physalin B

-continued physalin C physalin D physalin E physalin F physalin G

-continued physalin H physalin I physalin J physalin K physalin L

-continued physalin M physalin N physalin O physalin P physalin Q

-continued physalin R physalin S

Despite an improved isolation route to obtain physalins is provided by the present invention, conventional methods may also be used to obtain physalins from leaves and stems of *Physalis* species. It is important to emphasize that the process of the invention is simplified as compared with the known methods which involve several steps dealing with column chromatography.

Roots, and epigeal parts of *Physalis* spp. were collected in order to obtain physalins.

After being collected, roots or epigeal parts of *P. angulata* may be cut in small pieces and ground in a mixer. Crude extract is treated with an aqueous or alcoholic solvent in a suitable extractor, at room or higher temperature, the later by heating for at least 24 hours. Suitable alcoholic solvents include, but are not limited to methanol, ethanol, 1-propanol, 2-propanol, iso-butanol, sec-butanol and the like. The alcoholic extract when tested for anti *T. cruzi* activity showed 100% of mortality. The aqueous or organic extract is further evaporated and the syrup material (residue) is washed with a suitable non-polar organic solvent which, may include but is not limited to, chloroform, dichloromethane, dichloroethane, diethyl ether, toluene, and other non-polar organic solvents known to those skilled in the art. Then, the soluble fraction is partially evaporated and poured over a layer of silica H (gel). The extraction is performed by using a polarity gradient of organic solvents $S_1 < S_2 < S_3 < S_4$, i.e. the polarity degree increases from $S_1$ to $S_4$.

After filtration, the $S_2$ fraction (intermediary polarity) is treated by a further chromatographic step. The physalins came out with, for example, $S_1/S_3$ or $S_2/S_3$ fraction depending on the physalin required.

The withasteroids compounds obtained from roots, leaves and stems of *Physalis* spp. and other closely related genera of the Solanaceae family may be characterized by physicochemical means, e.g. spectroscopic methodology, using no more than routine experimentation.

The isolation process of the present invention has the following advantages: (1) it involves quite simpler and faster procedures; (2) it is particularly useful in developing countries due to its lower cost; and (3) it reduces product losses during the whole process because there are less chromatography steps.

The following examples are illustrative of the present invention and represent preferred embodiments. Those skilled in the art may know, or be able to find using no more than routine experimentation, other appropriate materials and techniques, such as the mentioned extracting substances and measuring methods.

EXAMPLE 1

Isolation of Physalins from *Physalis* spp. Roots 330 g of dried roots of *P. angulata* were cut in small pieces, ground and extracted with ethanol by heating in a Soxhlet extractor. The obtained extract was concentrated to dryness under reduced pressure and the resulting syrup material was washed with chloroform, in a proportion of about 3 to 5 times of the obtained weight. Then, the soluble fraction was partially evaporated and poured over a layer of silica H (gel) for filtration using, in a sequential fashion, hexane, dichloromethane, ethyl acetate and methanol as solvent extractor.

EXAMPLE 2

Isolation of Physalin B from *Physalis* spp. Roots

The dichloromethane fraction obtained in example 1 was treated again in a chromatographic column with silica G (gel). Physalin B was eluted with an ethyl acetate-hexane gradient and recrystallized.

EXAMPLE 3

Characterization of Physalin B

Physalin B was characterized using no more than routine spectroscopic methodology and the data obtained are shown below.

Physalin B has a melting point in the range of 235–237° C. It shows a molecular ion peak at m/z 510 (M+) and its $^1$H NMR (200 MHz) DMSO-$d_6$ spectrum presents signals at $\delta$ 5,88 ($H_2$, dd, J=10 Hz) and $\delta$ 6,90 ($H_3$, dd, J=10 Hz) for the same olefinic protons. Those values represent the absorptions of the hydrogen atoms linked to $C_2$ and $C_3$ which are attached to A ring. Three methyl groups are showed at $\delta$ 1,19 ($H_{19}$, s); $\delta$ 1,88 ($H_{28}$, s) and $\delta$ 1,26 ($H_{21}$, s). A pair of signals at $\delta$ 3,67 (d,J=13 Hz) and $\delta$ 4,32 (dd, J=13, 2 Hz) could be attributed to the methylene protons at C-27, confirming the oxyrane bridge at $Cl_4$—O—$C_{27}$. The hydroxylproton at $\delta$ 6,27 ($H_{13}$, s) and a doublet at $\delta$ 5,68 ($H_6$, dd) were a good tool to make sure that the molecule is physalin B. $^{13}$C NMR (54 MHz) in DMSO-$d_6$, showed twenty six signals. The missing two carbons from the $C_{28}$ structure, is due to the solvent, dimethyl sulfoxide that enveloped them at the range between 40 to 37 ppm. The peaks at 209,2 ppm ($C_{15}$); 203,3 ppm ($C_1$); 171,0 ppm ($C_{18}$) and 167,1 ppm ($C_{26}$) correspond to carbonyls from: ketone, ketone $\alpha$–$\beta$ unsaturated, two lactones (furan and pyrane rings).

The signals at 126,8 and 146,1 ppm are due to the methylene $C_2$ and $C_3$ in the double bond of A ring, and the signals at 135,5 and 123,3 ppm are from carbons 5 and 6 of B ring.

All the signals obtained from DEPT technique led us to the conclusion that the proposed compound is physalin B.

EXAMPLE 4

Isolation of Physalin D from *Physalis* spp. Roots

The material obtained in example 1 was treated again in a chromatographic column with silica G (gel) by using a chloroform/ethyl acetate gradient. Physalin D was obtained in the eluent fraction 1:1 v/v.

EXAMPLE 5

Characterization of Physalin D

Physalin D was characterized using no more than routine spectroscopic methodology and the data obtained are shown below.

Physalin D has a melting point 242–245° C. It shows a molecular ion peak at m/z 544 (M+,3%); 125 (M-419, 100%). Its $^1$H NMR (200 MHz) DMSO-$d_6$ spectrum are expressed in $\delta$ units and presented the following results: the protons attached to C-2 and C-3 show signals at 5,67 dd ($J_{2,3}$=10) 6,58 ddd ($J_{3,2}$=10) and a singlet at 4,13 corresponds to the hydrogen of hydroxyl group. A multiplet is showed at 3,49 for the proton attached at C-6, while the second hydroxyl group absorbs as a doublet at 4,55. It was possible to distinguish two hydrogen atoms linked to carbon 12 with signals at 1,48 (dd) $\beta$ and 2,13 (d). The three methyl groups ($CH_3$) absorb at 1.12, 1.18, 1.16 as a singlet for C-19, C-21 and C-28 respectively. All these values correspond to the literature data for physalin D.

Figure 1:
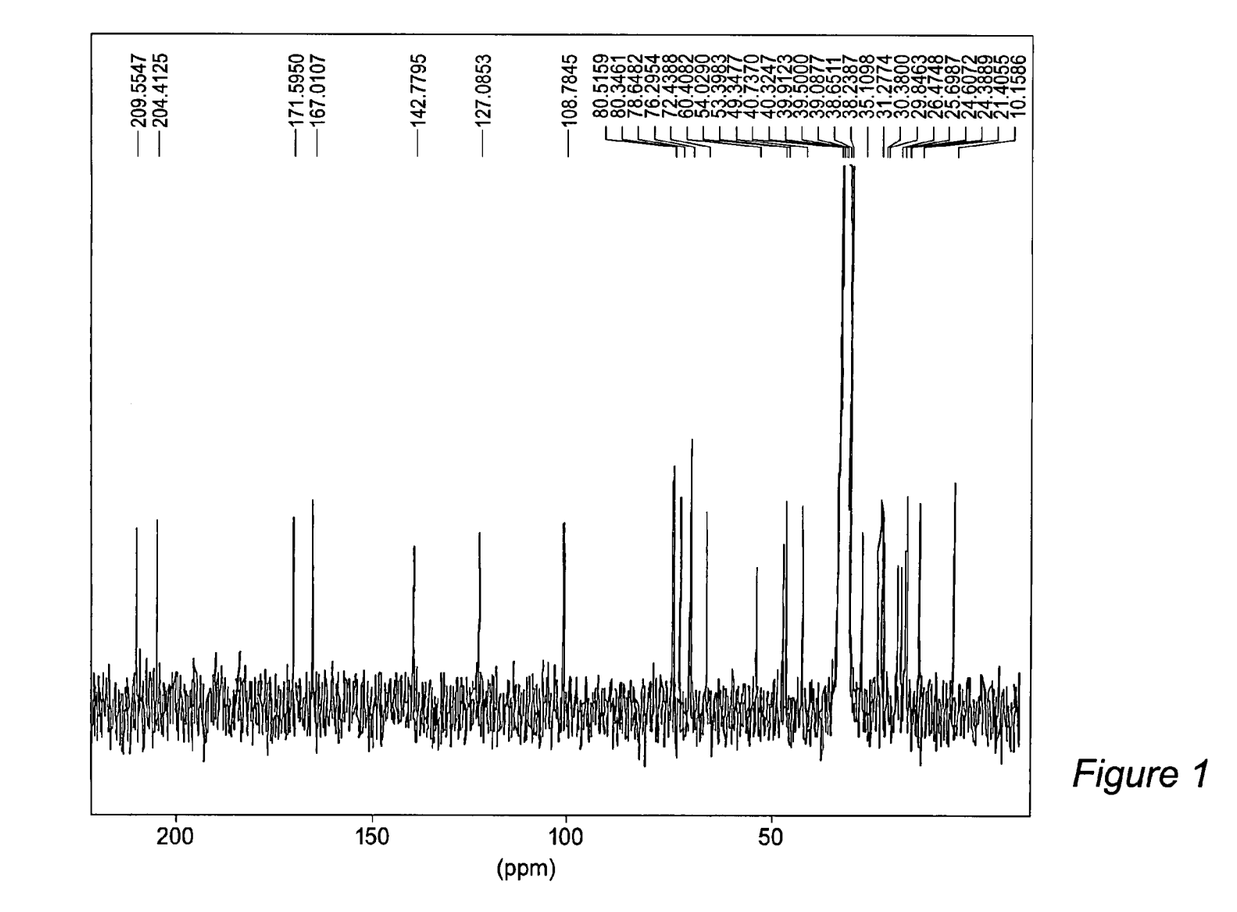
FIG. 1: shows the $^{13}$C NMR spectrum of physalin D.
Figure 2:
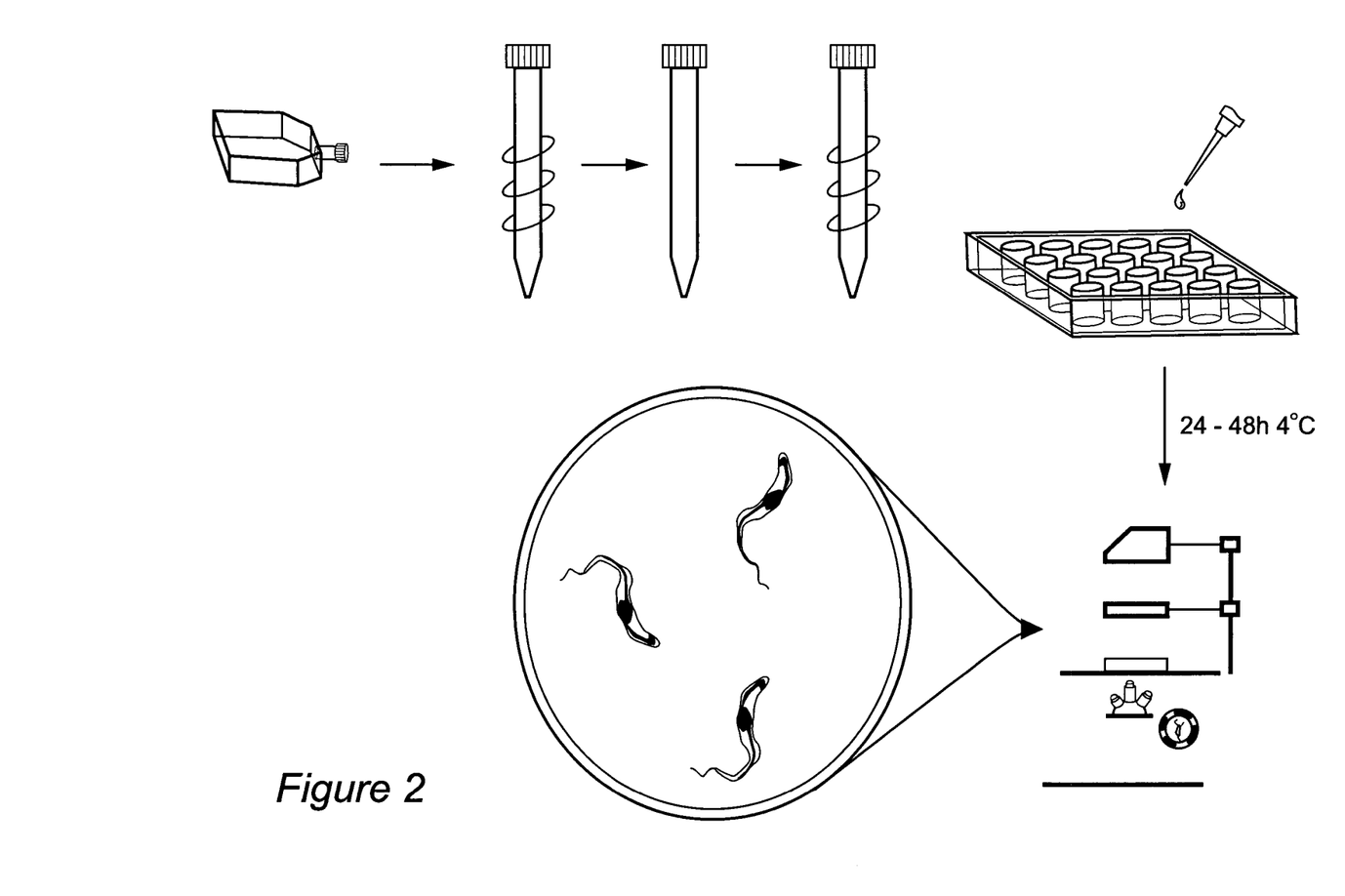
FIG. 2: illustrates the protocol to determine the in vitro trypanocidal activity of the physalins of the present invention.

It must be emphazised that physalin's D $^{13}$C NMR is described for the first time (see FIG. 1).

The $^{13}$C NMR spectrum of physalin D in DMSO-$d_6$ (54 MHz) presents peaks at 209,64 ppm for the carbonyl carbon at C-15; 204,52 ppm for the carbon C-1; 171,68 and 167,12 ppm for the carbons attached to quaternary center of the two lactone rings C-18/C-26; 142,89 and 127,16 ppm for the double bond C-2 and C-3 of Aring. The signals at 106,87 ppm correspond to (C-14); 80,60 (C-20); 80,40 (C-17); 78,75 (C-13); 76,38 (C-22); 72,52 (C-6); 60,49 (C-27); 54,11 (C-16); 53,48 (C-10); 49,43 (C-25); 35,19 (C-8); 31,36 (C-23); 30,46 (C-24); 29,93 (C-9); 26,56 (C-4); 25,78 (C-12); 24,69 (C-11); 24,27 (C-28); 21,49 (C-21) and 13,24 ppm to the carbon attached at position 19.

EXAMPLE 6

Pharmacological Tests of Physalins B and D

In vitro studies using pure physalins are carried out with trypomastigotes of *Trypanosoma cruzi*.

*T. cruzi* Y strain is maintained in MK2 strain cell culture in a RPMI medium+10% bovine fetal serum, at 37° C., under 5% $CO_2$. This material is centrifuged during 15 minutes at 1500 rpm. Afterwards, the material is maintained in rest at 37° C. for 2 hours. The supernatant is centrifuged again during 30 minutes at 3000 rpm. The trypomastigotes ($5\times10^5$/well) in RPMI medium with 10% bovine fetal serum and antibiotic are incubated in wells with different concentrations of physalin B or physalin D. After 24–48 hours, the viable parasites maintained at a temperature of 4° C. are counted. Each experiment was carried out in triplicate. The results are shown below.

TABLE I

In vitro antitrypanosomial activity of Physlins B and D

| Substance | Dose | Contact Period (hours) | Mortality of Parasite (%) |
|---|---|---|---|
| Physalin B | 2.5 mg/ml | 24 | 100 |
| Physalin B | 2.5 mg/ml | 48 | 100 |
| Physalin D | 40 μg/ml | 24 | 100 |
| Physalin D | 40 μg/ml | 48 | 100 |

As showed in Table I, parasite mortality is obtained after 24 hours when dealing with physalin B at a concentration of 2,5 mg/ml. Moreover, 100% of mortality is obtained after 24 hours by using only 40 μg/ml of physalin D.

These results are very significant if we consider the low concentration used, the mortality of the parasite (100%) and the efficacy of the operation time, i.e. 24 hours.

EXAMPLE 7

In Vivo Test with Experimental Animals Infected with *T. cruzi* Y Strain

Several samples from *P. angulata* L. extract were used in this experiment. Fractions obtained from the process for isolating the physalins were also used. Serum trypomastigotes were used to evaluate the trypanocidal activity of the *P. angulata* extract and physalins of the present invention.

Groups of three mice were intraperitoneally inoculated with $10^4$ parasites (serum trypomastigotes). During 10 days, these animals were daily, since the day before infection, treated with 20 mg/animal of (a) methanolic extract obtained from the fruit of *P. angulata* L.; (b) physalin mixture (physalins B, D, G, H and L) obtained from the leaves of *P. angulata* L.; and (c) ethanolic extract obtained from the stem-bark of *P. angulata* L. The treatment was orally applied.

Preparations (a) and (c) were diluted with 5% alcaholic solution containing 0.5% of polyoxyethylenesorbitol monolaurate.

Three mice used as controls received the same treatment but without the active substance ((a), (b) or (c) preparations).

An additional group of three infected mice was treated with a known trypanocidal drug (Rochegan™). The quantity of this drug applied to each animal was the same as the above mentioned preparations (a), (b) and (c). (*P. angulata* L. extracts and physalins).

After 10 days, all mice were examined to evaluate their parasitemia (the presence of parasites in the blood) levels. Table II presents the results.

TABLE II

Treatment of *T. cruzi* infected mice with *P. angulata* extracts or fractions thereof (physalins).

| *P. angulata* L. Extract or Fractions therof | Residual Parasitemia (%) |
|---|---|
| Physalin mixture (physalins B, D, G, H and L) obtained from the leaves of *P. angulata* | 33 |
| Methanolic extract obtained from the fruit of *P. angulata* | 35 |
| Ethanolic extract obtained from the stem-bark of *P. angulata* L | 16 |

From Table II, it can be concluded that the best efficacy performance (84%) was obtained when ethanolic extract from the stem-bark of *P. angulata* L. is applied in the treatment. The second best result (efficacy of 67%) is in the treatment with physalin mixture (physalins B, D, G, H and L) from the leaves of *P. angulata* L. The treatment with methanolic extract from the fruit of *P. angulata* L. showed an efficacy of 65%.

EXAMPLE 8

In Vitro Test to Evaluate the Antileishmanicidal Activity of Physalin B

Stationary phase promastigotes of *Leishmania amazonensis* were obtained from parasite cultures in LIT medium with 10% bovine fetal serum. The assays were standardized in plates with 96 wells. Promastigotes were plaque harbored, in triplicate, in 100 μl of LIT medium. 10 μl of physalin B solution and 10 μl of a positive control (Amphotericin B) are added to the wells. Several dilutions were used. Parasite viability was determined after incubation with MTT by reading the absorbance at 570 nm in ELISA Microplate.

100% of parasite mortality was obtained when 20 μg/ml of physalin B was used.

EXAMPLE 9

Evaluation of the Antileishmanicidal Activity of Physalin B in in Vitro Infection Assay by Using Peritoneal Macrophages Peritoneal macrophages were incubated during 2 hours at 37° C. in 24 wells plates with laminas. After washing to remove non-bound cells, the wells were incubated with stationary phase promastigotes of *Leishmania amazonensis* (parasites/macrophages in a ratio of 10:1). After 18 hours, the cultures were washed to remove the free parasites. After 24 hours, physalin B solution is added to the wells. The laminas are collected, fixed with methanol and dyed with Giemsa. The infection level was determined by counting parasite quantity and the infected macrophages percentage.

100% in vitro reduction in the infection of peritoneal macrophages was obtained when 10 μg/ml of physalin B was used.

EXAMPLE 10

In Vitro Tests to Evaluate the Immunosuppresive Properties of Physalin B

The immunosuppresive properties of physalin B were evaluated by simulating the responses of the immune system against invading organisms and toxic molecules produced by them.

Figure 3A:
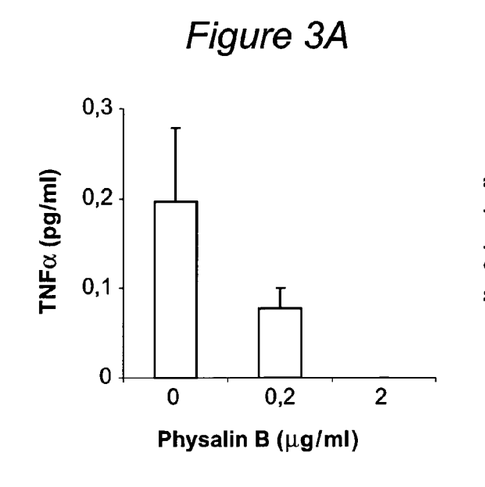
FIG. 3: shows the inhibitory properties of physalin B concerning to TNFα and IL-6 production by macrophages.
Figure 3B:
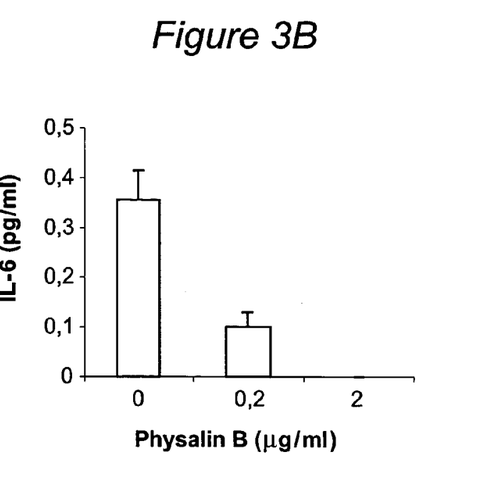

In a first test, thyoglycollate-elicited peritoneal macrophages were stimulated with LPS (500 ng/ml) in the presence of various concentrations of physalin B. Cell-free supernatants were collected 4 hours after stimulation and tested for TNα and IL-6 production by ELISA. FIGS. 3A and 3B show the inhibitory properties of physalin B concerning to TNFα and IL-6, respectively, production by macrophages.

Figure 4:
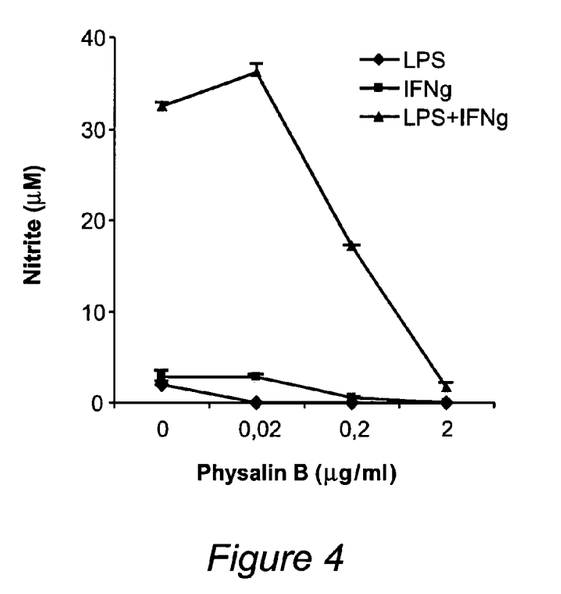
FIG. 4: shows the inhibitory properties of physalin B concerning to nitric oxide production by macrophages.

In a second test, thyoglycollate-elicited peritoneal macrophages were stimulated with LPS (500 ng/ml), IFNγ (5 ng/ml), or IFNγ +LPS in the presence of various concentrations of physalin B. Cell-free supernatants were collected 24 hours after stimulation and tested for nitrite production by Griess assay. FIG. 4 shows the inhibitory properties of physalin B concerning to nitric oxide production by macrophages.

Figure 5:
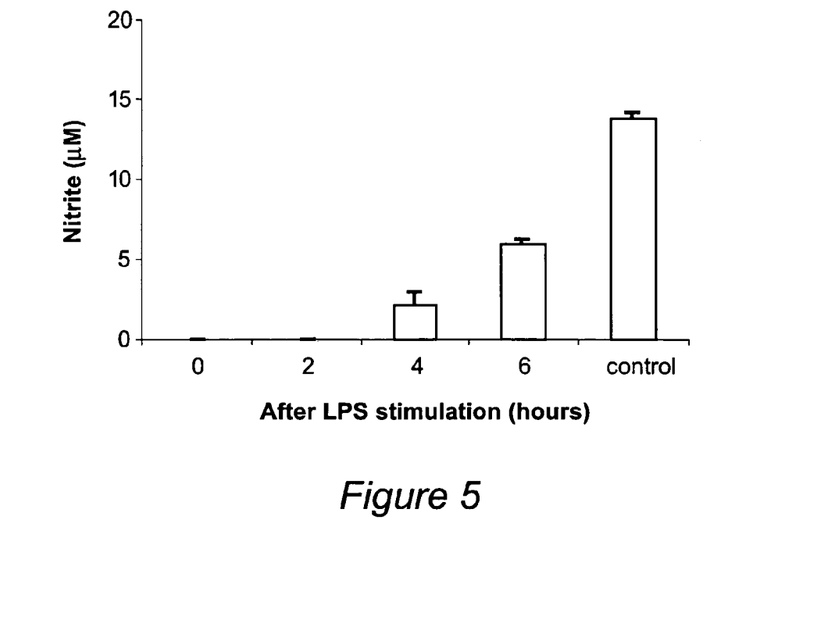
FIG. 5: illustrates the time-dependence of the inhibition of nitric oxide production by physalin B.

In a third test, thyoglycollate-elicited peritoneal macrophages were stimulated with LPS (500 ng/ml)+IFNγ (5 ng/ml). Physalin B (2 μg/ml) was added 0, 2, 4 and 6 hours after IFNγ+LPS stimulation. Cell-free supernatants were collected 24 hours after stimulation and tested for nitrite production by Griess assay. IFNγ+LPS was used as control. FIG. 5 illustrates the time-dependence of the inhibition of nitric oxide production by physalin B.

Figure 6:
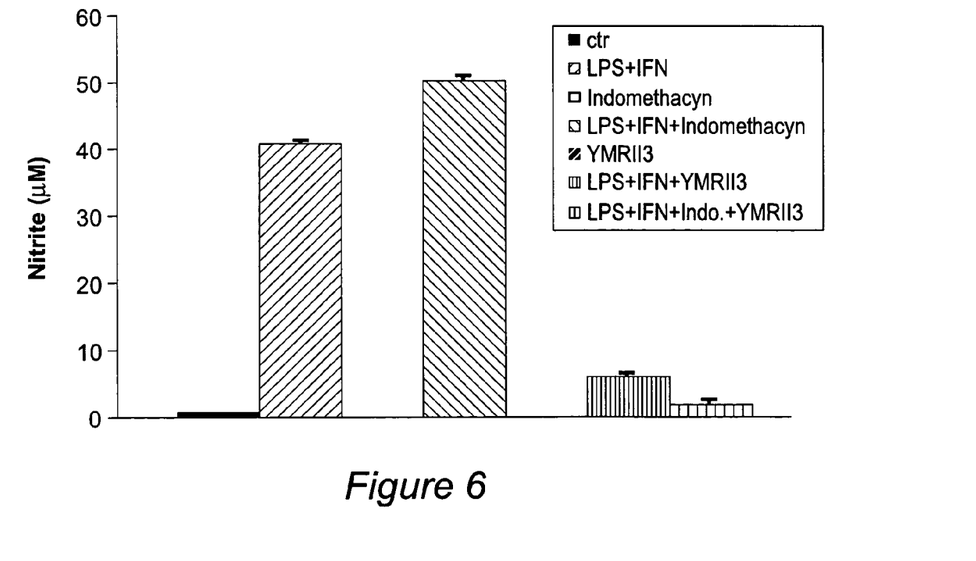
FIG. 6: illustrates the behavior of the inhibition of nitric oxide production induced by physalin B in the presence of indomethacyn.

In a fourth test, thyoglycollate-elicited peritoneal macrophages were stimulated with LPS (500 ng/ml)+IFNγ (5 ng/ml) in the presence of physalin B (2 μg/ml) or indomethacyn (1 μg/ml). Cell-free supernatants were collected 24 hours after stimulation and tested for nitrite production by Griess assay. FIG. 6 demonstrates the fact that the addition of indomethacyn does not block the inhibition of nitric oxide production by physalin B.

Figure 7:
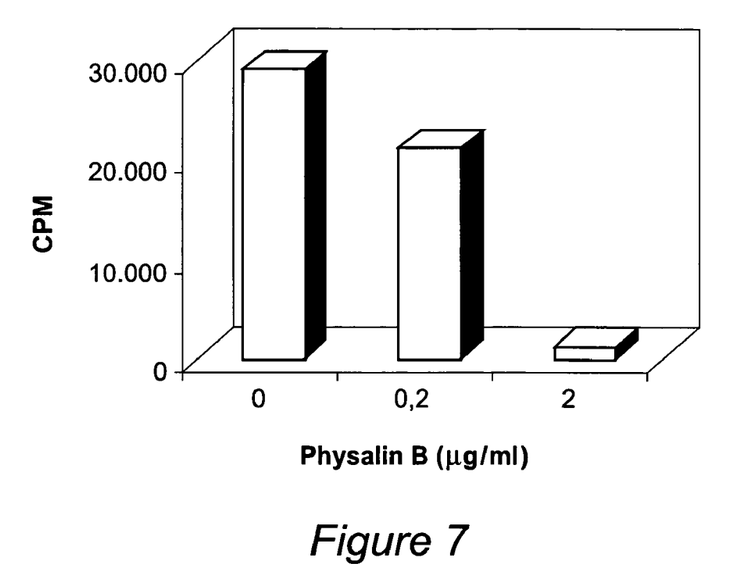
FIG. 7: illustrates the inhibition of ConA-stimulated splenocytes proliferation by physalin B.

In a fifth test, BALB/c spleen cells were stimulated with ConA (1 μg/ml) in the presence of several concentrations of physalin B. After 24 hours, cultures were pulsed with $^3$H thymidine. Proliferation was assessed by measurement of thymidine uptake. FIG. 7 demonstrates the fact that physalin B inhibits proliferation of ConA stimulated splenocytes.

Figure 8:
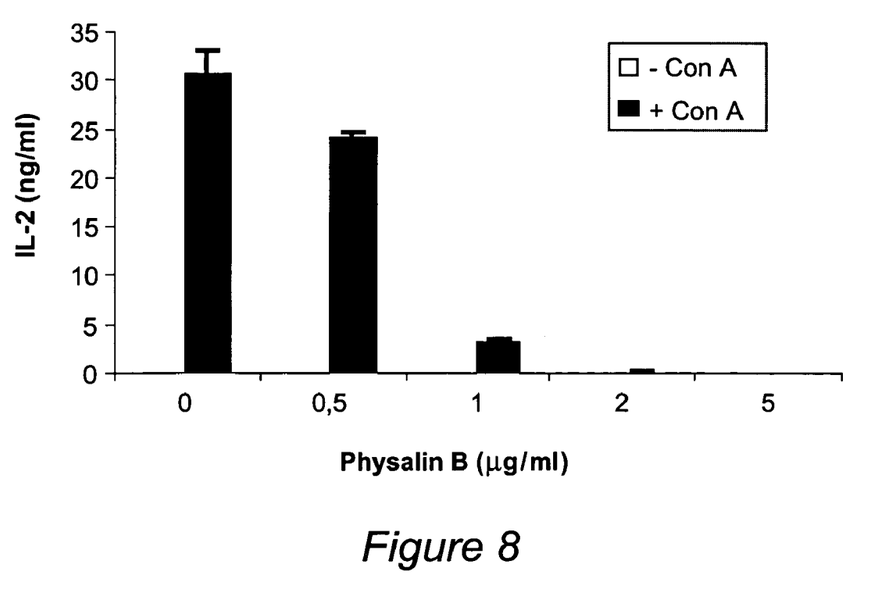
FIG. 8: shows the inhibition of IL-2 production by physalin B in response to ConA-stimulated splenocytes proliferation.

In a sixth test, BALB/c spleen cells were stimulated with ConA (1 μg/ml) in the presence of several concentrations of physalin B. Cell-free supernatants were collected 24 hours after stimulation and tested for IL-2 production by ELISA. FIG. 8 demonstrates the fact that physalin B inhibits IL-2 production by ConA stimulated splenocytes.

Figure 9A:
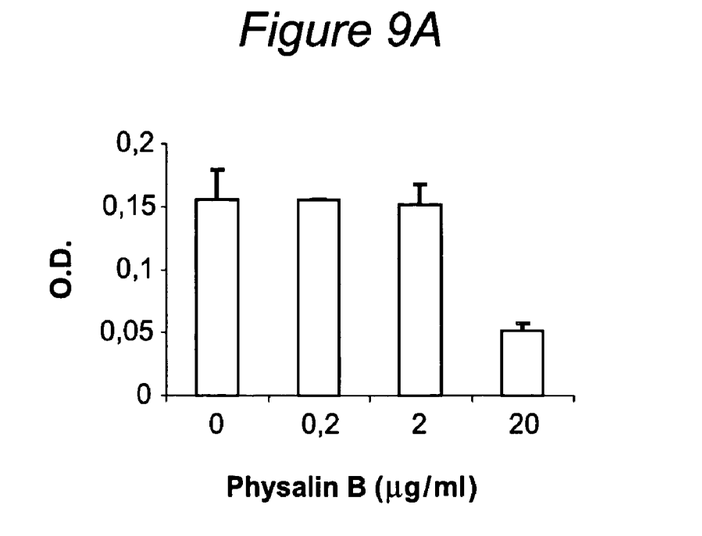
FIG. 9: illustrates the viability of macrophages and splenocytes incubated with physalin B.
Figure 9B:
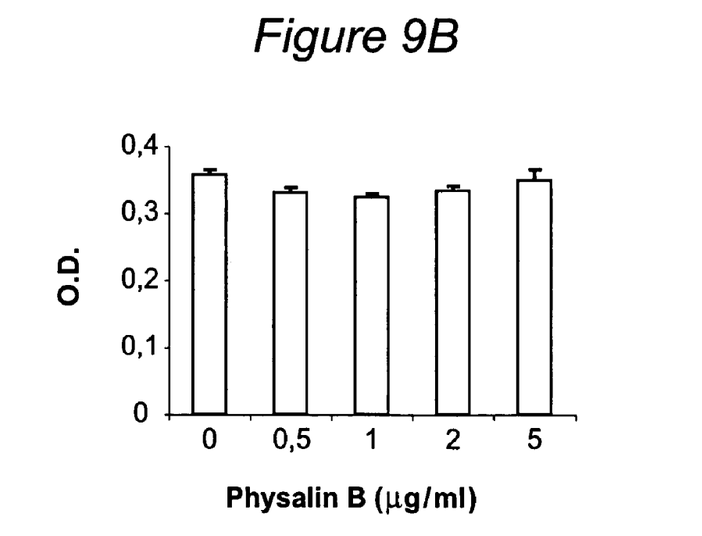

In the last test, BALB/c spleen cells or thyoglycollate-elicited peritoneal macrophages were cultured in the presence of several concentrations of physalin B. After one day (FIG. 9B) or three days (FIG. 9A) of culturing, plates were pulsed with MTT. Cell-viability was evaluated 2 hours later by optical density measuring at 570 nm. In this test, it is demonstrated that physalin is non-toxic in vitro at concentrations below 5 μg/ml.

What is claimed is:

1. A method of treating a person having a disease caused by a protozoa comprising administering to said person a composition comprising at least one physalin and a carrier.

2. The method of claim 1 wherein said composition is a pharmaceutical composition and said carrier is a pharmaceutically acceptable carrier.

3. The method of claim 1 wherein said disease is Chagas Disease or Leishmaniasis.

4. The method of claim 1 wherein said physalin is physalin B.

5. A method of treating a person having a disease caused by a protozoa comprising administering to said person a composition comprising an alcoholic steroid extract from a *Physalis* and a carrier.

6. The method of claim 5 wherein said composition is a pharmaceutical composition and said carrier is a pharmaceutically acceptable carrier.

7. The method of claim 5 wherein said disease is Chagas Disease or Leishmaniasis.

8. The method of claim 5 wherein said *Physalis* is a *P. angulata*.

9. A method of treating a person having a disease caused by a protozoa comprising administering to said person a composition comprising an aqueous steroid extract from a *Physalis* and a carrier.

10. The method of claim 9 wherein said composition is a pharmaceutical composition and said carrier is a pharmaceutically acceptable carrier.

11. The method of claim 9 wherein said disease is Chagas Disease or Leishmaniasis.

12. The method of claim 9 wherein said *Physalis* is a *P. angulata*.

* * * * *